United States Patent [19]

Mattson et al.

[11] Patent Number: 4,663,772
[45] Date of Patent: May 5, 1987

[54] BONE MINERAL ANALYSIS PHANTOM

[75] Inventors: Rodney A. Mattson, Mentor; Leslie J. Williams, Richmond Hts., both of Ohio

[73] Assignee: Picker International, Inc., Highland Hts., Ohio

[21] Appl. No.: 782,010

[22] Filed: Sep. 30, 1985

[51] Int. Cl.$^4$ ............................................ G01D 18/00
[52] U.S. Cl. ........................................ 378/18; 364/414; 378/207
[58] Field of Search ................... 378/18, 207, 901, 5; 364/414

[56] References Cited

U.S. PATENT DOCUMENTS

| | | | |
|---|---|---|---|
| 3,010,223 | 11/1961 | Alderson | 378/18 |
| 3,944,830 | 3/1976 | Dissing | 378/55 |
| 4,233,507 | 11/1980 | Volz | 378/207 |
| 4,352,020 | 9/1982 | Horiba et al. | 378/207 |

*Primary Examiner*—Carolyn E. Fields
*Assistant Examiner*—Constantine Hannaher
*Attorney, Agent, or Firm*—Fay, Sharpe, Fagan, Minnich & McKee

[57] ABSTRACT

A phantom (FIG. 1) has a bone mineral standard (B) surrounded by tissue equivalent material (A) with a plurality of different cross sections. The phantom is disposed in an image region (44) of a tomographic scanner (FIG. 2). Scans are conducted through a plurality of different cross sections of the phantom to reconstruct a plurality of phantom image representations (62). The plurality of phantom image representations are stored by size in a correction memory (70). Thereafter, a patient is disposed on a patient table (50) in the image region and an image is taken through the patient's midsection between the L2 and L5 vertebrae. A patient image representation is reconstructed and stored in an image memory (64). A slice size calculation circuit (72) determines the size of the patient slice. The correction memory is addressed with the calculated size to retrieve the phantom image representation of the most similar size. An image correction circuit (74) calibrates the patient image representation in accordance with the retrieved phantom image representation.

18 Claims, 2 Drawing Figures

BONE MINERAL ANALYSIS PHANTOM

BACKGROUND OF THE INVENTION

The present invention pertains to the art of medical diagnostic imaging. It finds particular application in the calibration of tomographic scanners in conjunction with the diagnosis of osteoporosis and will be described with particular reference thereto. It is to be appreciated, however, that the invention may find further application in conjunction with other calibrations of tomographic scanners and other medical diagnostic equipment.

Osteoporosis is a disease of long duration which is characterized by a bone mineral loss. The trabecular bone, which has a turnover rate about eight times higher than cortical bone, has been shown to be a sensitive early indicator of bone mineral loss. One method of monitoring for bone mineral loss has been to examine the spine, which is approximately 65% trabecular bone with an x-ray tomographic scan. The x-ray absorption characteristics of the trabecular bone and the reconstructed image are indicative of bone mineral content or density of the trabecular bone. One of the problems which has been encountered with x-ray tomographic scans of the trabecular bone has been calibrating the CT numbers or gray scale of the resultant image with sufficient precision to measure the amount of mineral loss accurately or to detect small mineral losses.

One solution for calibrating the gray scale images is set forth in U.S. Pat. No. 4,233,507 issued Nov. 11, 1980 to Donald J. Volz. In the Volz technique, calibration samples or phantoms are mounted in the patient supporting surface such that the calibration samples are imaged concurrently with the selected portion of the spine. This enables the gray scale or Hounsfield numbers for an imaged area of the spine to be compared with the known Hounsfield numbers for the calibration samples. However, the Volz techique has inherent inaccuracies in the calibration attributable to alterations in the beam caused by body tissues surrounding the spine.

The accuracy of the mineral content is determined by the accuracy of the CT numbers for the selected scanner and the chemical composition of the imaged bone tissue. Because the density of fat is less than that of soft tissue, it reduces the measured CT number by about 12 Hounsfield units per 10% of fat by weight. This produces an erroneous decrease in the measured bone mineral concentration. Concentrations of fat in the vertebral body of up to 40% have been reported. To reduce the magnitude of the CT number alteration attributable to fat, dual energy CT scanning techniques have been used.

The image reconstruction algorithms, x-ray spatial intensity compensation filters, x-ray beam filters, and x-ray beam hardness and scatter correction methods differ among various tomographic scanners. Commonly, scanner performance has been optimized by the use of empirical corrections to the above parameters to provide a flat response to water or tissue equivalent phantoms. These empirical corrections, in many instances, have not been linear to retain quantitative reconstructions over the entire field of view. These common, non-linear quantitative corrections in many instances are not constant for all body dimensions and x-ray excitation conditions. In particular, the x-ray beam quality is different for rays emerging through the center and the periphery of large bodies as contrasted with small body sections. This beam quality difference results in variations of the CT numbers for identical bone mineral materials.

This variation or shift in the CT numbers of otherwise identical bone mineral materials attributable to the amount and composition of surrouding soft tissue is uncorrected in the Volz technique. The Volz bone mineral reference samples are disposed peripherally where they are irradiated by off-focal radiation which has not passed through the same volume of soft tissue as the radiation passing through the spine. The peripheral, off-focal radiation may also introduce additional errors attributable to less accurate corrections made by shaped x-ray filters and compensators to off-focal radiation.

These problems become particularly acute when multiple energies of radiations are used. In particular, the volume of surrounding soft tissue, has relatively little effect on high energy radiation; whereas, the surrounding tissue more significantly affects low energy radiation. Thus, the body fat calibration corrections become particularly complex when utilizing a dual energy tomographic reconstruction technique, as is conventionally used to correct for the effects of the presence of the unknown amount of fat that has replaced tissue in the regions of interest.

The present invention contemplates a new and improved calibration method and apparatus which overcomes the above referenced problems and others to calibrate the CT numbers in the region of the spine more accurately.

SUMMARY OF THE INVENTION

In accordance with one aspect of the present invention, a phantom is provided for calibrating CT scanners for bone mineral examinations. The phantom includes a housing having a tapered side wall extending between first and second ends. The housing side wall defines a first, smaller generally ovoid cross section adjacent the first end and a second, larger generally ovoid cross section adjacent the second end. A plurality of intermediate generally ovoid cross sections which are larger than the first cross section and smaller than the second cross section are defined therebetween. A generally cylindrical bone mineral standard extends longitudinally between the first and second ends. In this manner, any one of the plurality of intermediate cross sections are imageable in the CT scanner to provide a calibration reference for patients of comparable dimension.

In accordance with another aspect of the present invention, a tomographic scanner with bone mineral calibration is provided. The scanner includes a source of penetrating radiation for providing a generally planar beam of penetrating radiation. A radiation detecting means detects the penetrating radiation impinging thereon. A gantry means mounts the radiation source and the radiation detection means across an image region from each other such that the radiation beam traverses the image region and impinges upon the radiation detection means. A phantom has a generally cylindrical bone mineral standard extending longitudinally therethrough and a tissue equivalent material therearound. The tissue equivalent material is constructed to have a plurality of transverse cross sections. A phantom positioning means positions each of a plurality of the transverse cross sections in the image region. The radiation moving means moves at least the beam relative to the phantom such that the radiation traverses the image region along a plurality of directions. An image reconstruction means reconstructs a representation of the material density in the image region from radiation detected by the radiation detection means.

In accordance with a more limited aspect of the present invention, the scanner also includes a mineral density correction memory for storing the image reconstructions from radiation detection data collected through each of a plurality of the phantom cross sections. A correction means corrects at least one of the detected radiation data and the reconstructed image representation of a patient with one of the material density representations stored in the correction memory. In this manner, the CT number for an imaged patient is corrected and calibrated in accordance with the stored data from the phantom. Optionally, specific information pertaining to bone mineral density that has been extracted from reconstructed images may also be saved in memory.

In accordance with yet another aspect of the present invention, a method of bone mineral examination is provided. A phantom which has a generally cylindrical bone mineral standard extending longitudinally therethrough and a plurality of tissue equivalent transverse cross sections is disposed in a tomographic scanner. An image of the phantom is taken through at least one of the transverse cross sections and stored. A patient whose bone mineral is to be examined is disposed in the scanner and an image of a patient transverse slice is reconstructed. The patient image is combined with a stored phantom image taken through a transverse section of the phantom of comparable dimensions with the patient transverse slice to calibrate the CT numbers of the patient.

One of the advantages of the present invention is that it enables accurate examinations for bone mineral content or loss of a patient to be made with a tomographic scanner.

Another advantage of the present invention is that it provides the accurate calibration for dual energy examinations.

Another advantage of the present invention is that it facilitates early detection of the onset of osteoporosis.

Still further advantages of the present invention will become apparent to those of ordinary skill in the art upon reading and understanding the following detailed description of the preferred embodiment.

BRIEF DESCRIPTION OF THE DRAWINGS

The invention may be embodied in various parts or arrangements of parts or in various steps or arrangements of steps. The drawings are only for purposes of illustrating a preferred embodiment and are not to be construed as limiting the invention.

DETAILED DESCRIPTION OF THE PREFERRED EMBODIMENT

Figure 1:
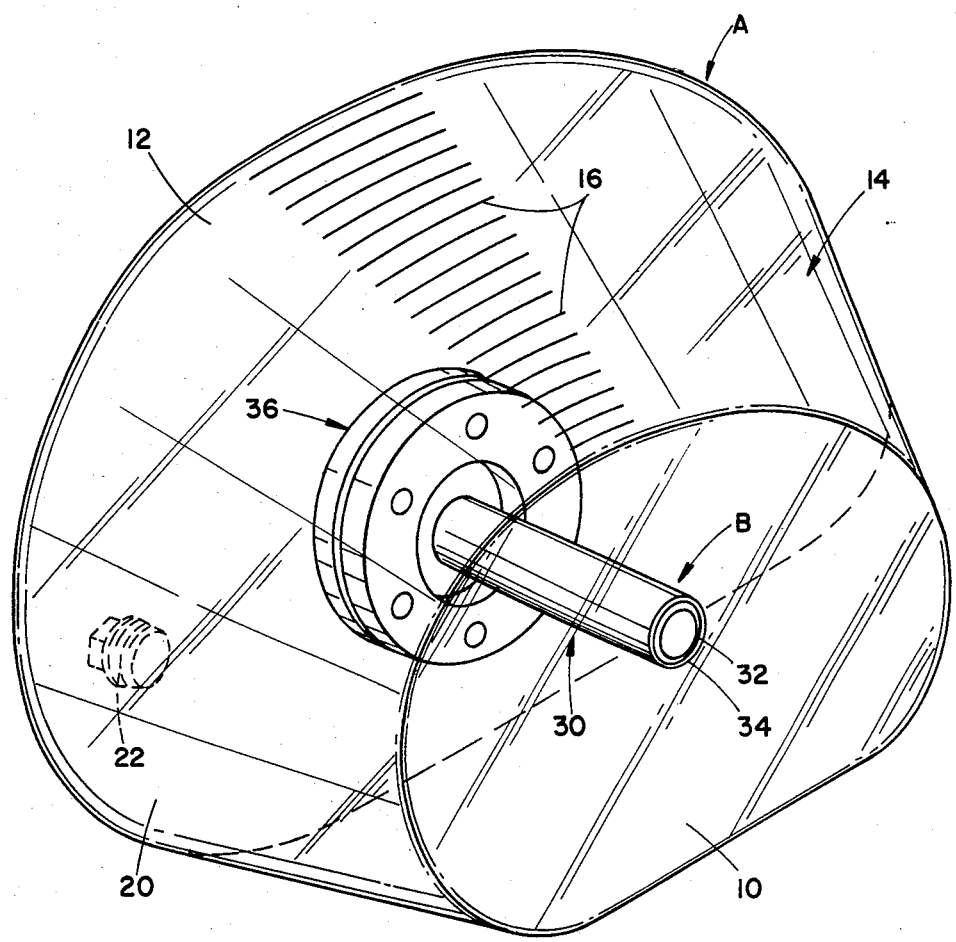
FIG. 1 is a perspective view of a phantom in accordance with the present invention; and, FIG. 2 is a diagrammatic illustration of a tomographic scanner in accordance with the present invention.

With reference to FIG. 1, the phantom includes a tissue equivalent portion A and a bone mineral equivalent portion B. The tissue equivalent portion has a first end 10 which has a first or smaller generally ovoid cross section. The first end is shaped in conformity with the cross section of a smaller or skinnier patient's mid-section adjacent the L2 to L5 vertebrae. The tissue equivalent portion A further has a second end 12 which has a second or larger generally ovoid cross section. The second cross section conforms to the shape of a larger or fatter patient adjacent the L2 to L5 vertebrae. A central portion 14 of the tissue equivalent structure has a plurality of intermediate cross sections which are larger than the first or smaller cross section and smaller than the second or larger cross section. In the preferred embodiment, the intermediate cross sections are arranged in a continuum. However, discrete cross sections may be provided. A plurality of markings 16 provide a means for indicating the transverse cross section at discrete intervals along the central portion 14.

In the preferred embodiment, the tissue equivalent portion includes an outer, hollow housing 20 which has an access aperture 22 therethrough to enable the interior to be filled with water or other tissue equivalent fluids. Optionally, the tissue equivalent portion could be constructed of or filled with a tissue equivalent plastic or other solid or semi-solid material.

The bone mineral equivalent portion B in the preferred embodiment is a cylindrical bone mineral calibration standard 30 of a bone mineral tissue mimicking substance. In the preferred embodiment, the standard has a tubular core 32 of a trabecular bone mimicking material. A peripheral coating 34 of a cortical bone simulating material may extend around the central core 32 to simulate the effects of beam hardening in the spine due to the denser cortical bone. Suitable bone mineral mimicking substances are available from RMI, Inc. of Madison, Wis. A flange 36 mounts the bone mineral standard 30 in approximately the same position relative to the tissue equivalent portion A as the spine is located in the human body. In the preferred embodiment, the bone mineral standard is about nine centimeters from the base and parallel thereto.

Because the position of the spine and its diameter do not change significantly in persons of different girth, the bone mineral standard 30 is a fixed distance from the base and is not tapered. However, tapers and angular orientations may optionally be provided where appropriate. Moreover, additional layers or fillings of other materials, such as materials which simulate fat tissue, may also be incorporated in the bone mineral standard. As yet another option, an acutal section of a spinal column may be mounted in the phantom.

Figure 2:
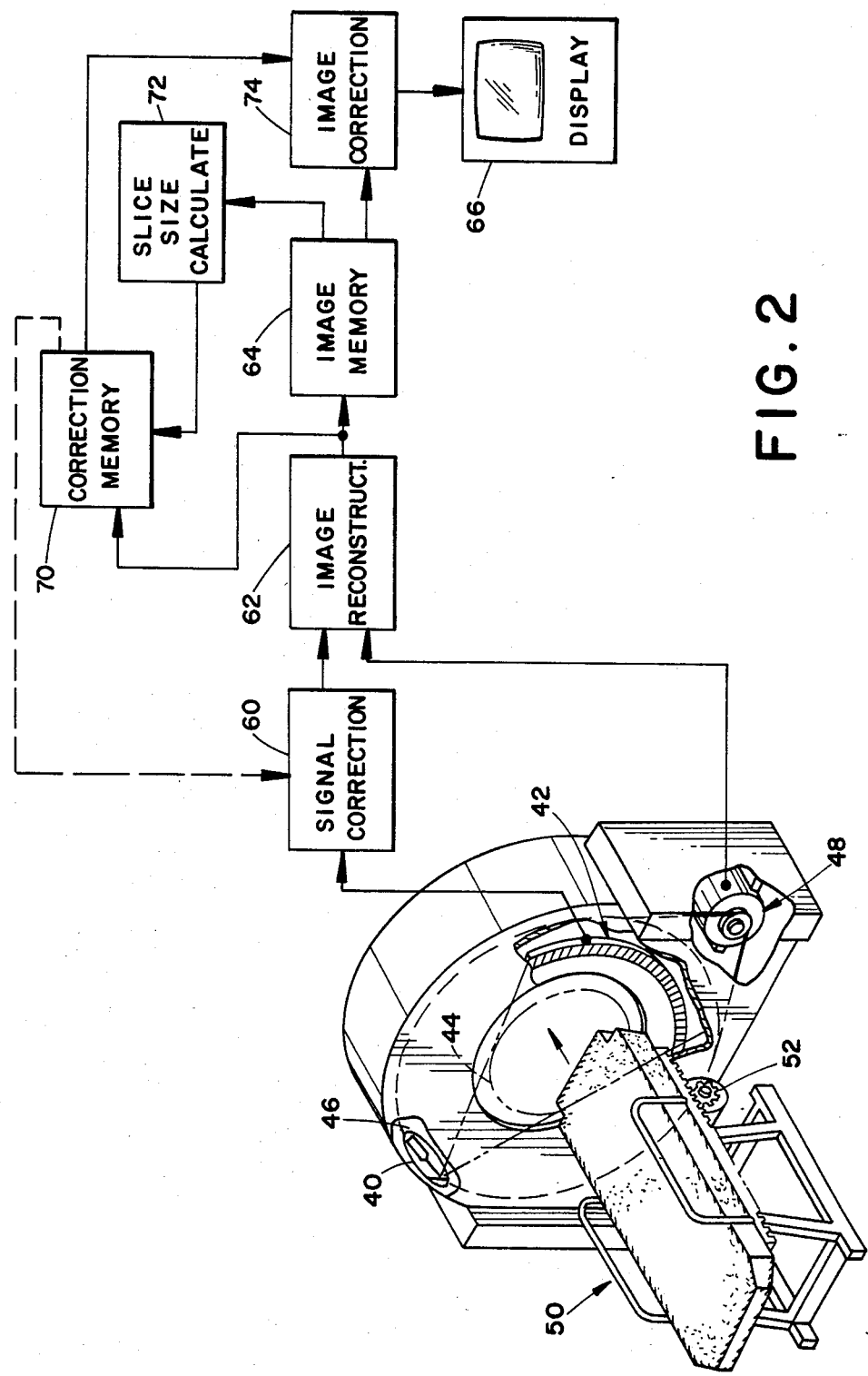

With reference to FIG. 2, a tomographic scanner includes a source 40 of penetrating radiation, such as an x-ray tube. A radiation detection means 42 receives penetrating radiation which has traversed an image region 44 and a patient or other examined object disposed therein. In the preferred embodiment, the radiation detection means is a bank of scintillation crystals and photodiodes. However, other electronics which convert received radiation into electrical signals which vary in accordance with the relative intensity thereof may be used. A gantry or rotating frame means 46 supports at least the radiation source 40 for rotation about the image region 44 under the control of an electric motor or other rotating means 48.

A patient support table 50 is mounted to support the phantom, a patient, or other object to be examined within the image region 44. A phantom and patient positioning means 52 selectively positions the phantom, patient, or other examined object longitudinally through the image region.

The detection means 42 is connected with signal correction circuitry or means 60 which performs conventional corrections on the radiation detector data, such as beam hardness corrections, electronic filter compensations, and the like. Moreover, the signal correction means 60 may correct the radiation detector data in accordance with the data stored from previously scanned phantom sections as is explained herein below. An image reconstruction means 62 reconstructs a representation of an image of the slice of the phantom, patient, or other object disposed in the image region 44. A convolution and back projection or other known image reconstruction system may be utilized. The reconstructed image representation includes a grid of numbers which represent radiation intensity or, conversely, radiation attentuation at a corresponding pixel of the image region. The reconstructed image of a patient under examination is stored in an image memory 64 for display on a video monitor 66 or other suitable display means or for storage on tape or other electronic storage mediums. Optimally, only selected information from the image representation may be stored or displayed.

Prior to imaging a patient, the phantom described in conjunction with FIG. 1 is positioned on the patient table and examined in the image region. At least preselected information from reconstructed image representations of the phantom taken at a plurality of cross sections is stored in a correction memory 70. The size of the cross section which each image represents may be input into the correction memory directly from the positioning means 52, may be manually entered, or may be calculated by a size calculating means 72. The size calculating means determines the diameter, girth, or other dimension of a transverse slice stored in the image memory 64.

After the correction memory 70 has been loaded with the phantom image representations or at least selected information therefrom, a patient is placed on the patient table and positioned such that the image region is disposed between the L2 and L5 vertebrae. A patient image representation is reconstructed from the radiation data to produce an uncorrected patient image in the image memory 64. The slice size calculation means 72 determines the diameter or other appropriate measurement of the size of the imaged patient slice. The size calculation means addresses the correction memory 70 to retrieve the phantom image representation information which corresponds to the most similarly sized cross section of the phantom. An image correction circuit or means 74 adjusts the patient image representation from the image memory 64 in accordance with the addressed phantom image representation information in the correction memory 72 to adjust or calibrate the gray scale or CT numbers with precision. Optionally, the signal correction means 60 may correct the radiation detector data in accordance with the data from the correction memory 70. The display means 66 displays the corrected image or may display the CT numbers for one or more selected pixels thereof. Although described in functional modules, the functions are preferably performed in full or in part by a suitably programmed processor or computer.

In the preferred embodiment, the phantom is utilized to reload the correction memory 70 at the beginning of each period of operation. Optionally, the phantom may be used to reload the correction memory immediately before or after the examination of each patient. If the correction memory is reloaded immediately before or after each patient scan, then only the phantom portion which corresponds in size to the slice of the patient to be imaged need be examined. Moreover, it is to be appreciated that the data from high and low energy beams may be collected concurrently and processed either serially by the FIG. 2 circuitry or in parallel by duplicate circuitry.

The invention has been described with reference to the preferred embodiment. Obviously, alterations and modifications will occur to others upon reading and understanding the preceding detailed description. It is intended that the invention be construed as including all such alterations and modifications in so far as they come within the scope of the appended claims or the equivalents thereof.

Having thus described the preferred embodiment, the invention is now claimed to be:

1. A tomographic scanner with bone mineral calibration, the scanner comprising:

a source of penetrating radiation for providing at least one generally planar beam of penetrating radiation;

a radiation detection means for detecting penetrating radiation impinging thereon;

a gantry means for mounting the radiation source and the radiation detection means across an image region from each other such that the radiation beam traverses the image region and impinges on the radiation detection means;

a phantom having a generally cylindrical bone mineral standard extending longitudinally therethrough and a tissue equivalent material therearound, the tissue equivalent material having a plurality of transverse cross sections of different sizes;

a phantom positioning means for selectively positioning each of a plurality of the transverse cross sections in the image region;

a radiation moving means for moving at least the radiation beam relative to the phantom such that the radiation beam traversing the image region penetrates the phantom along a plurality of directions; and, an image reconstruction means for reconstructing a representation of material density in the image region from radiation detection data from the radiation detection means, the image reconstruction means being connected with the radiation detection means and the radiation moving means.

2. The scanner as set forth in claim 1 further including a bone density correction memory means for storing information from the material density representations representing each of the plurality of transverse cross sections through the phantom.

3. The scanner as set forth in claim 2 further including a correction means for correcting at least one of the radiation detection data and the material density representation of a patient with the information from one of the material density representations stored in the correction memory means.

4. A tomographic scanner with bone mineral calibration, the scanner comprising:

a source of penetrating radiation for providing at least one generally planar beam of penetrating radiation;

a radiation detection means for detecting penetrating radiation impinging thereon;

a gantry means for mounting the radiation source and the radiation detection means across an image region from each other such that the radiation beam traverses the image region and impinges on the radiation detection means;

a phantom having a generally cylindrical bone mineral standard extending longitudinally therethrough and a tissue equivalent material therearound, the tissue equivalent material having a plurality of transverse cross sections of different sizes;

a radiation moving means for moving at least the radiation beam relative to the phantom such that the radiation beam traversing the image region penetrates a selected phantom transverse cross sections along a plurality of directions;

a phantom positioning means for selectively positioning each of a plurality of the different sized phantom transverse cross sections in the image region to be irradiated by the moving radiation beams;

an image reconstruction means for reconstructing a representation of material density in the selected phantom transverse cross sections from radiation detection data from the radiation detection means;

a correction memory means for storing the reconstructed material density representations representing each of a plurality of the selected phantom transverse cross sections;

a size calculating means for calculating a dimension of an imaged slice of a patient; and, a correction memory addressing means for addressing the correction memory means to retrieve the stored reconstructed material density representation corresponding to a like size phantom cross section.

5. A radiographic scanner with bone mineral calibration, the scanner comprising:
   a source of penetrating radiation for providing at least one generally planar beam of penetrating radiation;
   a radiation detection means for detecting penetrating radiation impinging thereon;
   a gantry means for mounting the radiation source across an image region from the radiation detection means such that the radiation beam traverses the image region and impinges on the radiation detection means;
   a phantom including a hollow phantom housing having a tapered side wall extending between a first end and a second end, the phantom housing side wall defining a first, smaller, generally ovoid cross section adjacent the first end and a second, generally larger ovoid cross section adjacent the second end, the phantom housing having a continuum of intermediate cross sections between the first and second ends which intermediate ovoid cross sections are larger than the first cross section and smaller than the second cross section, the phantom further including a generally cylindrical bone mineral standard extending within the phantom housings between the first and second ovoid cross section;
   a radiation moving means for moving at least the radiation beam relative to the phantom such that the radation beam traversing the image region penetrates the phantom along a plurality of directions; and,
   an image reconstruction means for reconstructing a representation of material density in the image region from data collected by the radiation detection means.

6. The scanner as set forth in claim 5 wherein the phantom housing further includes access means for enabling the phantom housing to be filled with a tissue equivalent material.

7. The scanner as set forth in claim 5 wherein the bone mineral standard includes a first cylindrical portion which mimics the standards of trabecular bone mineral tissue and a surrounding layer which mimics cortical bone mineral tissue.

8. The scanner as set forth in claim 5 wherein the phantom housing has a continuum of intermediate cross sections between the first and second ends and further including a means for denoting cross sectional sizes along the intermediate housing portion.

9. A phantom for calibrating gray scale of tomographic scanner bone mineral examination images, the phantom comprising:
   a housing having a tapered side wall extending between a first end and a second end, the housing side wall defining a first, smaller generally ovoid cross section adjacent the first end, a second, larger generally ovoid cross section adjacent the second end and a plurality of intermediate ovoid cross sections which are larger than the first cross section and smaller than the second cross section therebetween;
   a generally cylindrical first bone mineral standard extending longitudinally generally between the first and second ends;
   a second bone mineral standard different from the first bone mineral standard extending circumferentially around the first bone mineral standard, such that any one of the first, second, and intermediate ovoid cross sections are imageable in a tomographic scanner to provide a bone mineral calibration reference.

10. The phantom as set forth in claim 9 wherein the housing is hollow and includes an access opening for receiving water or other tissue equivalent fluids therein.

11. The phantom as set forth in claim 10 wherein the housing defines a continuum of intermediate cross sections.

12. The phantom as set forth in claim 11 further including indicating means disposed along the housing to indicate cross sectional areas thereof.

13. The phantom as set forth in claim 9 wherein the first bone mineral standard mimics the characteristics of trabecular bones and wherein the second bone mineral mimics the characteristics of cortical bone tissue.

14. A method of tomographic scanning comprising:
   (a) positioning a phantom which has a generally cylindrical bone mineral standard extending generally longitudinally therethrough, a tissue equivalent material therearound, and a plurality of cross sections of different sizes in an image region of a tomographic scanner;
   (b) rotating a source of penetrating radiation to irradiate a planar slice of the phantom from a plurality of directions;
   (c) detecting radiation which has traversed the phantom slice;
   (d) reconstructing an image representation from the detected penetrating radiation;

(e) storing information from the phantom image representation;

(f) repeating preceding steps (b) through (d) with a mid-portion of a patient disposed in the image region to reconstruct an image representation of a planar slice through the patient's mid-section; and, (g) calibrating gray scale of the patient image representation with the phantom image representation information.

15. A method of tomographic scanning comprising:

(a) positioning a phantom which has a generally cylindrical bone mineral standard extending generally longitudinally therethrough, a tissue equivalent material therearound, and a plurality of cross sections of different sizes in an image region of a tomographic scanner;

(b) rotating a source of penetrating radiation to irradiate a planar slice of the phantom from a plurality of directions;

(c) detecting radiation which has traversed the phantom slice;

(d) reconstructing an image representation from the detected penetrating radiation;

(e) storing information from the phantom image representation;

(f) repeating steps (b) through (e) for a plurality of different cross sectional sizes of the phantom;

(g) repeating preceding steps (b) through (d) with a mid-portion of a patient disposed in the image region to reconstruct an image representation of a planar slice through the patient;

(h) determining a size of the imaged slice of the patient; and, (i) correcting gray scale of the patient image representation with information from the most similarly sized phantom image representation.

16. The method as set forth in claim 15 wherein the patient is imaged between the L2 and L5 vertebrae.

17. The method as set forth in claim 16 wherein the bone mineral standard mimics the characteristics of at least trabecular bone mineral tissue.

18. The method as set forth in claim 17 wherein the bone mineral standard further mimics the characteristics of surrounding cortical bone tissue.

* * * * *